US00PP34220P2

(12) United States Plant Patent
Shipley

(10) Patent No.: US PP34,220 P2
(45) Date of Patent: May 10, 2022

(54) ***SPHAERALCEA* PLANT NAMED 'ORANGE CRUSH'**

(50) Latin Name: ***Sphaeralcea ambigua* Gray**
Varietal Denomination: Orange Crush

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 0 days.

(21) Appl. No.: 17/300,552

(22) Filed: Aug. 16, 2021

(51) Int. Cl.
*A01H 5/02* (2018.01)
*A01H 6/60* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new and distinct *Sphaeralcea ambigua* named 'Orange Crush' is characterized by bright orange flowers that appear most heavily in winter to spring and with some flowers produced almost throughout the year. The plant has a dense appearance because of a high number of stems produced from a basal crown. The plant is about twice as wide as it is tall (1.3' tall×2.5' wide).

5 Drawing Sheets

Latin name: *Sphaeralcea ambigua* Gray.
Varietal denomination: 'Orange Crush'.

BACKGROUND OF THE INVENTION

*Sphaeralcea ambigua*, commonly called desert globemallow, is a perennial, herbaceous, shrub sized plant native from southern Utah through southern California, Arizona, Sonora and Baja Calif.. Desert globemallow has been used in Southwestern landscapes as seasonal color and although herbaceous, as a small shrub. The present invention relates to a new and distinct cultivar of desert globemallow. The cultivar resulted from a proprietary open pollinated breeding line selection which proved to be very compact and low growing in form with everblooming tendencies and is the object of this application. Both male and female parents were part of this breeding line, which contains considerable in-line diversity. Since the breeding line is seed harvested en masse and the seeds collected are mixed together, it is not possible to determine which individual plants were either the male or female parent.

SUMMARY OF THE INVENTION

Among the features that distinguish the new cultivar from all other available and commercial varieties of *Sphaeralcea ambigua* known to the inventor are the following combination of characteristics: plant smaller and shorter than is typical for the species with a low, dense, compact growth form, an everblooming tendency and bright orange flowers.

The propagation procedure is as follows: Three inch long herbaceous cuts are wetted with a 1:10 solution of Dip'N Gro™, then planted into peat media trays and then moved to a mist greenhouse at a commercial nursery near Sahuarita, Ariz. without bottom heat with air temperatures of 70-85° F. Cuts are misted every 20 minutes. Rooting is essentially completed within about 3 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Sphaeralcea ambigua* 'Orange Crush' growing near Sahuarita, Ariz., depicted in color as nearly correct as it is possible to make in a color illustration of the character.

DETAILED PLANT DESCRIPTION

Figure 1:
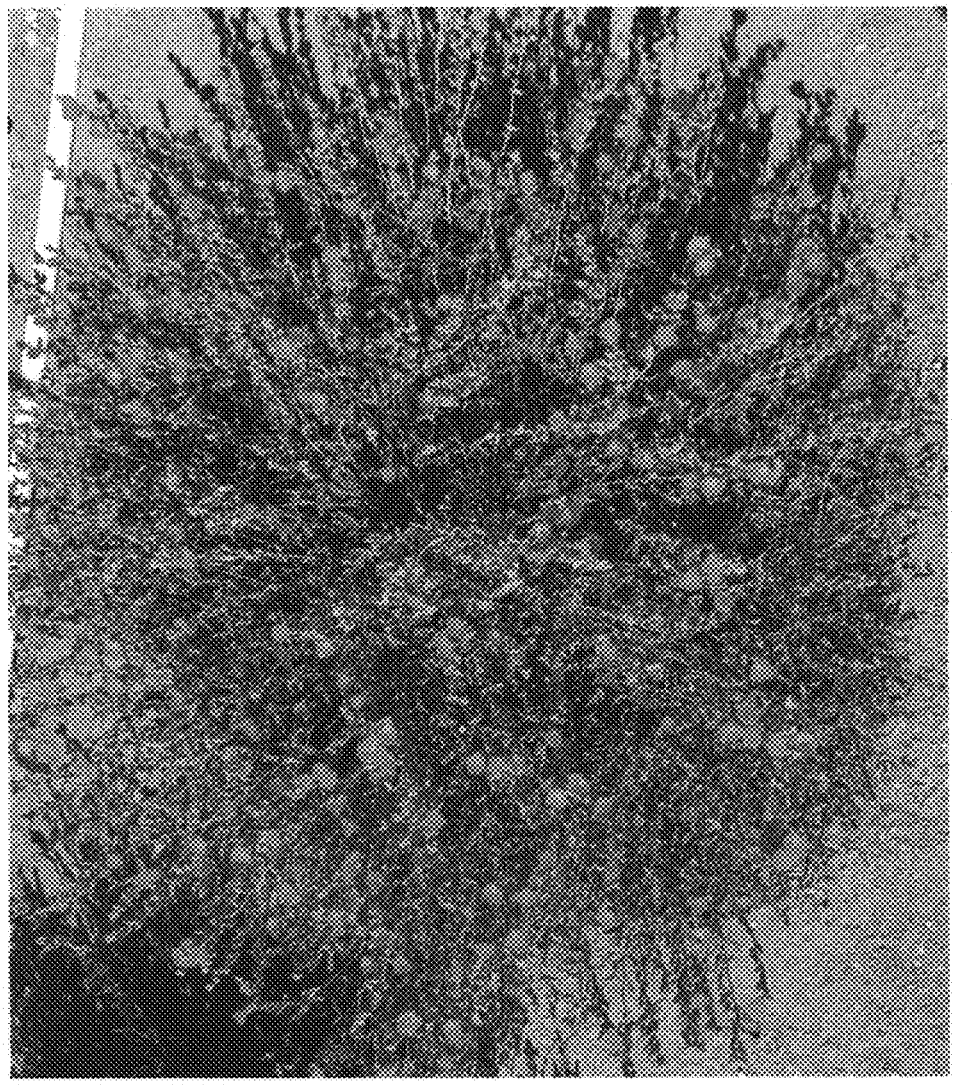
FIG. 1 shows *Sphaeralcea ambigua* 'Orange Crush' aged 2 years from cutting growing at a commercial nursery near Sahuarita, Ariz.
Figure 2:
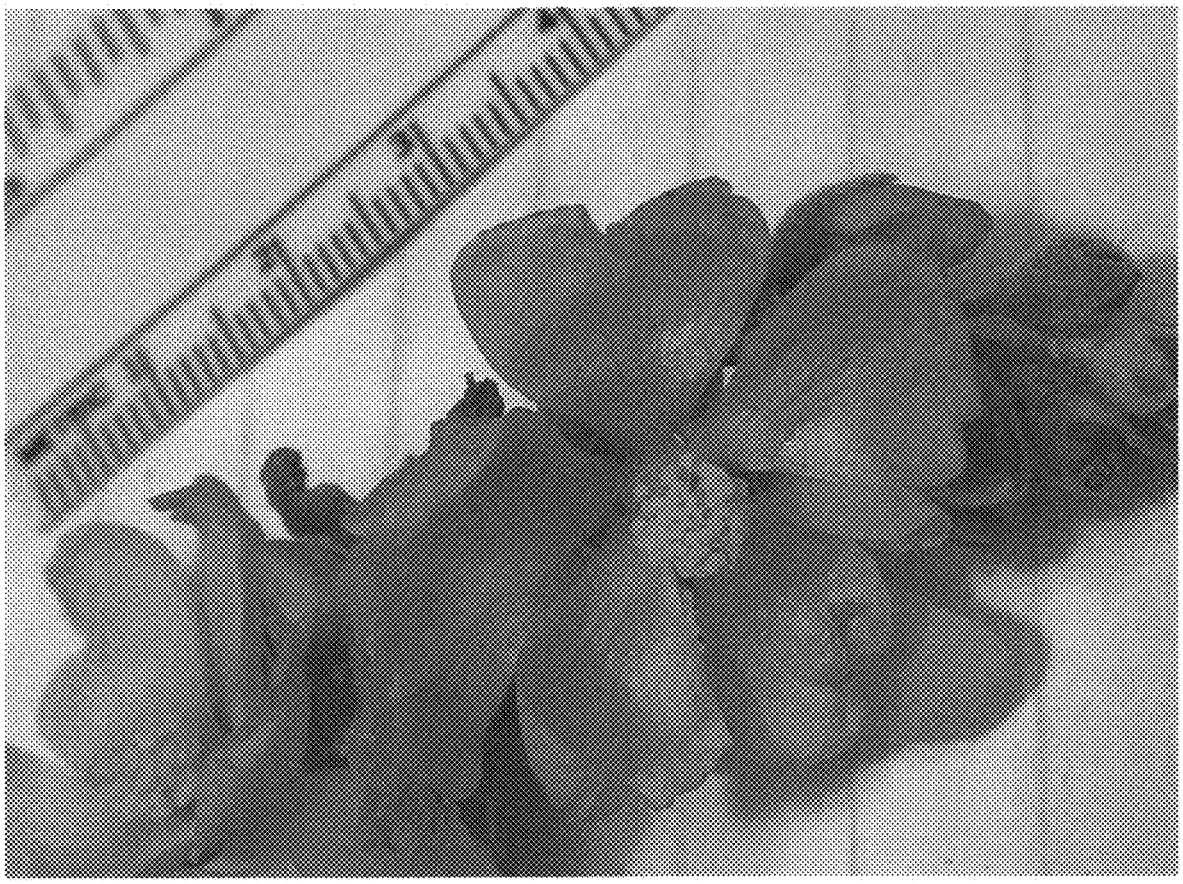
FIG. 2 illustrates flowers of *Sphaeralcea ambigua* 'Orange Crush'.
Figure 3:
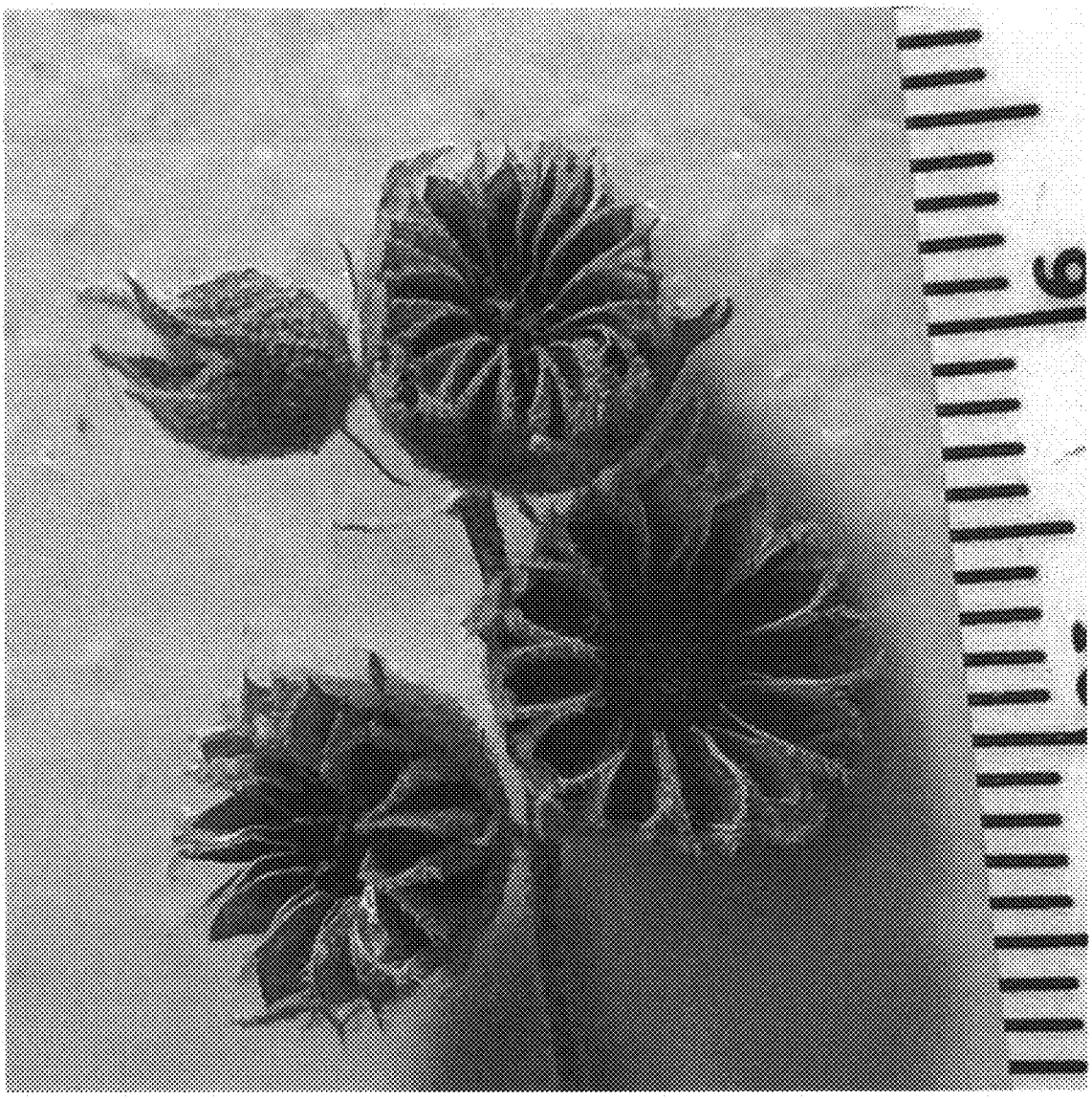
FIG. 3 shows the fruits of *Sphaeralcea ambigua* 'Orange Crush' fully matured at the time of dehiscence.
Figure 4:
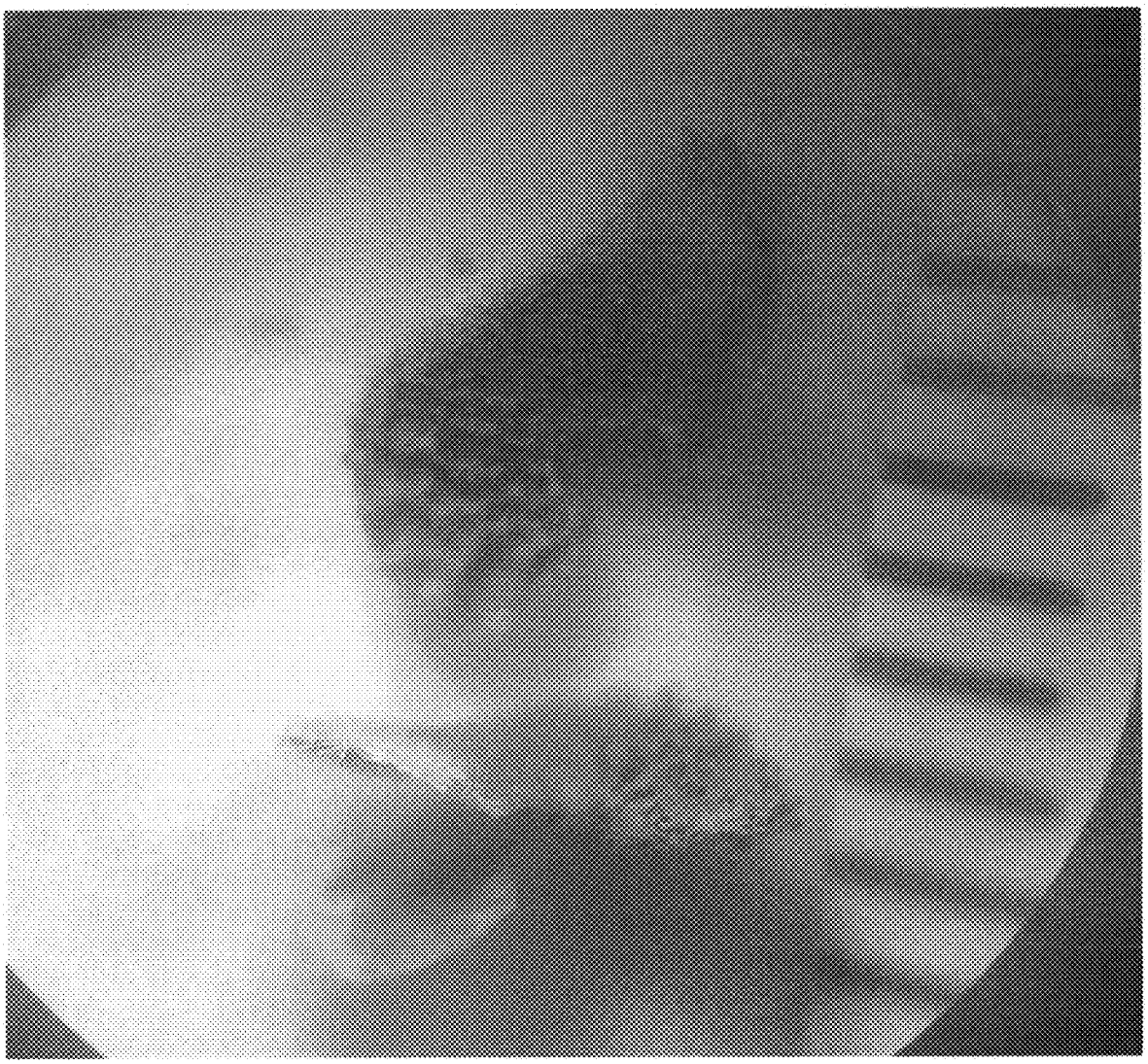
FIG. 4 shows 2 fruit segments of *Sphaeralcea ambigua* 'Orange Crush' just released from a dehisced capsule.
Figure 5:
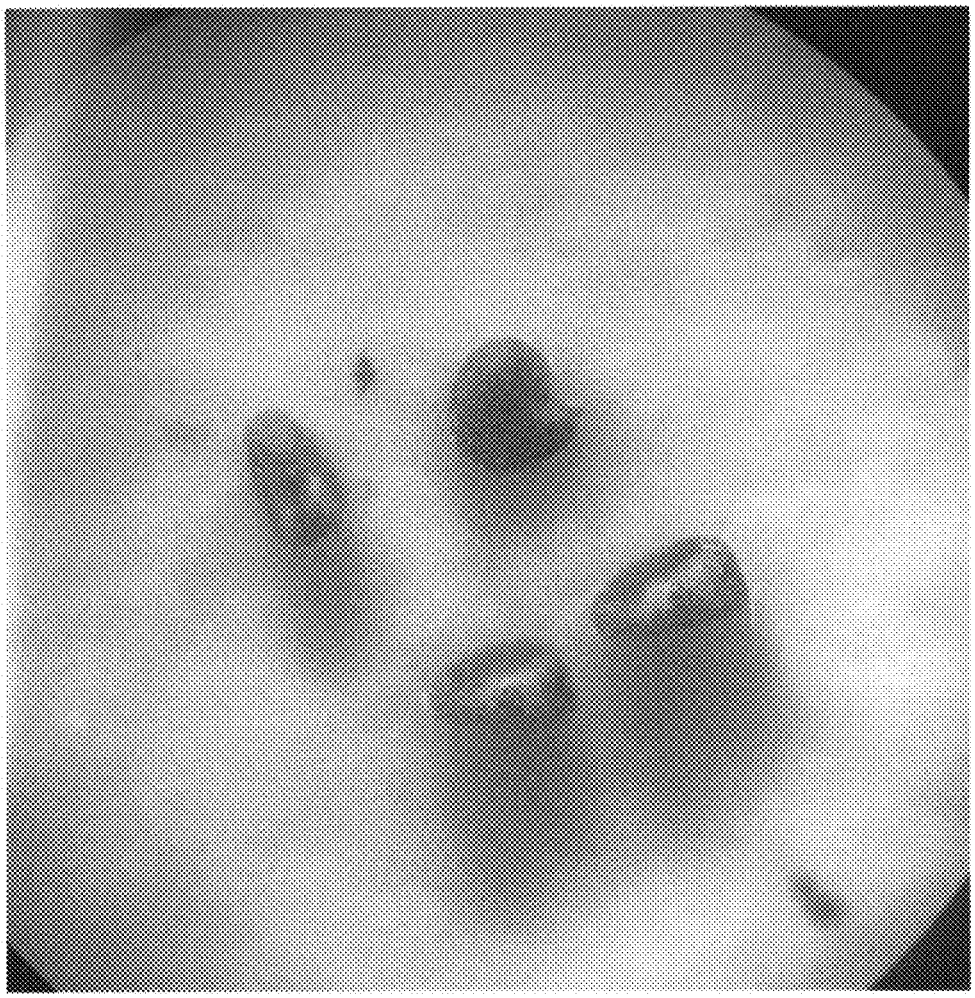
FIG. 5 illustrates the seeds of *Sphaeralcea ambigua* 'Orange Crush'.

The following is a detailed description of the new *Sphaeralcea ambigua* 'Orange Crush' plant based upon 2 year old plants propagated by cuttings growing under irrigation in the ground near Sahuarita, Ariz.

The following color descriptions are based upon the 5$^{th}$ edition R.H.S. Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Plants at age 2 years from cutting, growing in the ground with irrigation at a commercial nursery near Sahuarita, Ariz. measure about 1.3 foot tall×2.5 feet wide. Plant is evergreen with numerous (about 300) mostly unbranched herbaceous stems arising from a suffrutescent ground level crown (about 6 inches wide at age 2), which is formed by the growth of numerous short rhizomes. The stems terminate in thyrsoid inflorescences bearing from few to 30 or so flowers each depending upon the vigor and position of the stem bearing the inflorescence. Flowering is heaviest from winter through spring, although the cultivar shows everblooming tendencies with some flowers produced throughout the year.

Stems are 1-3 mm in diameter, tapering apically. Internodes measure 5-27 mm in length, being shortest near the inflorescence. The stems are terete and pubescent with stellate hairs (stem color 138B) Older stems exposed to the direct sun become blotched with color 185A on the sunward side.

Leaves are alternate, petiolate, covered with stellate hairs and ovate in overall shape. Axillary buds are obscure. The terete leaf petioles are covered with stellate hairs, colored 138B, and measure 12-28 mm long×1.0-1.2 mm in diameter. The petiole includes 2 pulvini, one just below the leaf blade and one at the stem attachment. These measure 2-3 mm in length, colored 145C. The pulvini are loosely covered in stellate hairs. The color change between the main body of the petiole and the pulvini is abrupt. The pinnately veined leaf blade is ovate in overall shape, but variably incised (between ¼ to ½ the distance from the leaf margin to the midrib) with 5-11 lobes. The apex of the leaf is acute. The leaf base is obtuse. The lobe apices vary from acute to obtuse, the longer lobes being acute and the shorter lobes varying from acute to obtuse. The longest lobes are at the base of the leaf. The adaxial surface of the leaf is covered with stellate hairs and the leaf surface is slightly indented above the leaf veins. The abaxial side of the leaf is covered with stellate hairs and the pinnate veins are raised above the general leaf surface. Both sides of the leaf and the veins are colored 189A.

Mature buds one day prior to anthesis measure 10 mm long×6 mm diameter and are ovoid in shape. The calyx extends and partially covers the corolla for about ⅔ of the bud length with the upper ⅓ being only the petals. The calyx is rounded at the base which constitutes about ⅓ the length of the bud. Five long triangular calyx teeth extend about ⅓ of the bud length mostly appressed to the corolla, but often slightly spreading near the apices of the teeth. The teeth also are apiculate near the apices. The calyx is canescent with stellate hairs. Calyx color is 194B, but this becomes increasingly mottled with 53B starting at the upper ⅓ to ½ of each tooth. The exposed corolla in bud is colored 31B. The petals in bud are spirally overlapped. The bud is subtended by three bracts attached just below the calyx. These bracts become fully desiccated several days earlier in bud development. The bracts and more details of the calyx are described with the open flowers.

Flowers: Flowers are bright orange, color 31B, measuring 28-32 mm wide. The terete pedicel measures 1.5-7.0 mm long×1 mm in diameter. The surface of the pedicel is densely covered with stellate hairs, pedicel color 194B. Flowers last 2 days. The spent flowers shrink and shrivel remaining attached to the developing fruit until the fruit approaches maturity.

The flower is subtended by three linear bracts located immediately below the calyx. These bracts dry out many days before anthesis but persist. Bracts measure 5 mm long×0.2 mm wide and are erratically shriveled. Bracts, color 164A, are covered with stellate hairs (NN155B).

Calyx measures 13-15 mm in diameter×6 mm long. Basal portion of the calyx is fused and rounded conical in shape. The abaxial surface is covered with white (NN155B), stellate hairs. This portion of the calyx is colored 194B. The basal portion of the calyx constitutes about ½ of the total calyx radius. The calyx divides into 5 free, spreading, long triangular, apiculate calyx lobes. These lobes measure 5 mm long×3 mm wide at the base of each lobe. The calyx lobes are covered with stellate hairs much like the fused portion of the calyx. The lower ½ to ⅔ of each lobe is colored 194B. Beginning at the upper ⅓ to ½ of each lobe color 53B appears as mottles scattered upon the lobe base color, these becoming gradually more prominent at the calyx lobe apices.

Petals are glabrous, obovate, terminally retuse, marginally entire, measuring 14 mm long and 13 mm wide. Of that length the basal 2 mm is colored 1C. At the 2 mm distance the color abruptly changes to 31B for the rest of the petal. Within the orange (31B) portion of the petals there are about 20 fine veins (color 32A) visible under magnification paralleling the petal margins. These veins are slightly raised adaxially, slightly indented abaxially. Interior and exterior petal colors are identical.

A fused staminal column (color 1C) is firmly attached to the petal bases and is immediately adjacent to the ovary. The staminal column is loosely covered in erratically spreading hairs, color 1B. The sticky pollen is commonly adhered to these hairs giving a first impression the hairs are glandular, which they are not. The base of the staminal column measures 3.3 mm in diameter. The column then tapers in the shape of a reversed trumpet to a diameter of 1.5 mm near the midpoint of the column. From there up to the base of the staminal cluster the column is relatively cylindrical. The column is 3.0-3.5 mm long below the staminal cluster. The cylinder continues for about 3 mm further supporting a stamen cluster where it gives rise to numerous filaments terminating in anthers. The staminal cluster is roughly spherical and measures from 3.0-4.5 mm in diameter. The staminal cluster contains numerous stamens estimated to be around 50 in number.

Stamens are 2.2 mm in length. The filament is about 1.5 mm long×0.2 mm in diameter, terete, glabrous, color 1C. Anthers are nearly spherical, measuring 0.7 mm in diameter, color 15B. Pollen is spherical, translucent, color 15B, measuring 40 μ in diameter.

The pistil measures 8.5 mm in length and is 2.5 mm in diameter at the ovary which is an oblate spheroid in shape. The ovary measures 2.5 mm wide×1.5 mm thick. The ovary (color 157A) is densely covered with stellate hairs. The hairs are colored 155D. The style (color 157D) is 3 mm in length, terete, glabrous, tapering from 0.5 mm in diameter just above the ovary to 0.33 mm at the point where the style disperses into spreading, terete segments that match the number of carpels (10-14). These sub-styles are about 3 mm in length including the stigmas and 0.1 mm in diameter, terminating in hemispherical stigmas measuring 0.15 mm in diameter and 0.08 mm in height. The stigmas are colored 69A. The sub-styles are colored 157D at the base but starting at the ⅔ distance from the base the color becomes increasingly mottled with 185B as the stigma is approached. At anthesis the tips of the sub-styles and stigmas project through the sides of the upper ¼ of the stamen cluster.

Inflorescence is a terminal thyrse with up to 30 flowers produced on each inflorescence. At mid bloom an average inflorescence measures 14-20 cm long×2.5-4 cm wide. The inflorescence occupies the upper ¼-½ of each stem. The terete peduncle measures 2 mm in diameter at its base tapering to 1 mm just below the upper flowers. Some of the few flowered peduncles are as thin as 1 mm in diameter at their base. The peduncle is covered with stellate hairs and is colored 194B. The hairs are colored 155C. The branches of the inflorescence alternate up the axis of the peduncle.

Nearly mature fruits (color 139C) are spherical, measuring 7 mm in diameter and height. Fruits have 10-14 carpels. The calyx lower half (color 138C) is clasping to the fruit. The calyx upper half is raised and incurved, the color 138C extending up to the midpoint of the calyx teeth, where some drying has taken place resulting in mottling of 53A on a background color of 161C.

The ripened mature fruit is a cupped, septicidal, apically disarticulating capsule (exterior color 199C) comprised of 10-14 carpels, each of which contains 1-2 seeds. At this stage, stellate hairs (color 161C) are still present on the fruit exterior, although many have fallen away. The carpel segments also dehisce loculicidally to about half of their length to produce 2 hatchet head shaped wings to allow wind dispersal. Ripe capsules vary in diameter from 6-13 mm and from 4-5 mm in thickness.

Fruit segments are overall reniform in shape except the wing end terminates in a hatchet shaped margin at that end. Fruit segments measure 5.5 mm long×3 mm wide×2.5 mm thick. The two wings of each segment flare laterally from the segment starting at the midpoint of the fruit segment. Their sides are smooth, puberulous with hairs colored 161C. the margins of each segment including the wing margins are covered with stellate hairs colored 161C. The lateral base of the segment which contains the seed(s) is glabrous and coarsely reticulate, the reticulum strongly raised, color N200A. The surface of the segment transitions abruptly from reticulate to smooth at the midpoint of the segment. The color of the wings is 200A at the wing base and gradually transitions to 199C at the wing margin. The wing interior is glabrous and colored like the exterior.

Seeds are reniform/orbicular in shape, tapering from a broad rounded end to a point located just above the hilum. The two flattened, slightly indented sides of the seed flare away from each other starting at the adaxial (hilum) side toward the abaxial (dorsal) side at an angle of about 30°. Seeds measure 1.2-1.4 mm long×1.0-1.1 mm wide×0.9 mm thick. The margin of the seed is covered with erratic/villous hairs variably colored from 158D to 161C. Hairs are most concentrated near the hilum. Seeds vary in color from N200A to N200B. The point on the seed near the hilum is a laterally compressed cone measuring 0.1 mm long×0.1 mm wide at the base×0.05 mm thick at the base, colored 161B. The hilum is round, 0.2 mm in diameter and colored 200A. The hilum is mostly obscured with villous hairs colored 161A.

*Sphaeralcea ambigua* 'Orange Crush' is hardy to at least 10° F. Rust fungi are reported to be a problem for the species, but the inventor has not seen this disease attacking this cultivar. No other insect or disease problems were noted.

COMPARISONS TO RELATED *SPHAERALCEA*

Compared the range of variation seen within the parental line, *Sphaeralcea ambigua* 'Orange Crush' is more compact and shorter relative to width. The uniquely large number of stems produced is distinctive relative to the range of variation seen within the parental line. Additionally, 'Orange Crush' has a strong everblooming tendency which has not been seen in other plants grown from the parental line.

There are several named cultivars in existence, none of them patented.

'Newleaze Coral' is listed as being 3-4' tall×3' wide and has coral red flowers and may be distinguished from 'Orange Crush' by both its upright growth form compared to low growing (about twice as wide as tall) for 'Orange Crush' as well as the distinctive flower color difference.

'Louis Hamilton' is another cultivar with red flowers. It can be distinguished from 'Orange Crush' by its flower color, taller growth and lower plant density than 'Orange Crush'.

'Papago Pink' is a cultivar with pink flowers and a growth form with height and width about equal (about 3 feet). 'Papago Pink' can be distinguished from 'Orange Crush' by its different flower color and more upright and open growth form.

Munro's Globe Mallow, *Sphaeralcea monroana* is sold by several nurseries, and while not a cultivar per se (apparently seed grown) and a different species of *Sphaeralcea* is included for comparison because of its flower color being like that of 'Orange Crush'. Munro's Globe mallow may be easily distinguished from 'Orange Crush' by its tall growth form (twice as tall as wide) as well as being a summer to late summer bloomer while 'Orange Crush' blooms heaviest in the winter and spring with scattered blooming throughout the year.

'Hot Pink' is another cultivar that grows about 3' tall and as wide with magenta flowers in late spring to summer. This cultivar may be distinguished from 'Orange Crush' by its more upright form, different flower color and different bloom season.

I claim:

1. A new and distinct *Sphaeralcea ambigua* plant named 'Orange Crush' substantially as described and illustrated herein.

* * * * *